United States Patent [19]

Fujita et al.

[11] Patent Number: 4,474,814

[45] Date of Patent: Oct. 2, 1984

[54] RADIOSENSITIZING NITROBENZOIC ACID AMIDE DERIVATIVES

[75] Inventors: Eiichi Fujita, Kyoto; Yoshimitsu Nagao, Uji; Tomoyuki Mori, Yokohama; Chieko Murayama, Zama; Tetsuji Asao, Tokushima, all of Japan

[73] Assignee: Taiho Pharmaceutical Company Limited, Tokyo, Japan

[21] Appl. No.: 444,339

[22] Filed: Nov. 23, 1982

[30] Foreign Application Priority Data

Nov. 26, 1981 [JP] Japan .................. 56-191228

[51] Int. Cl.³ .................. C07C 103/82; C07C 103/87; A61K 31/165
[52] U.S. Cl. .................. 424/324; 564/139; 564/157
[58] Field of Search .................. 564/139, 157; 424/324

[56] References Cited

U.S. PATENT DOCUMENTS

| | | | |
|---|---|---|---|
| 3,022,268 | 2/1962 | Armitage et al. | 564/157 X |
| 3,242,213 | 3/1966 | Preston et al. | 564/157 X |
| 3,499,031 | 3/1970 | Smith et al. | 564/157 |
| 4,009,208 | 2/1977 | Lesher | 564/157 X |
| 4,058,523 | 11/1977 | Mori et al. | 564/157 X |

OTHER PUBLICATIONS

Smithen et al., *Radiation Sensitizer*, pp. 22–38, (1982), ed. by Brady, Masson Publishing, (U.S.).
Stratford et al., Radiation Research 88, pp. 502–509, (1981).
Winkelmann et al., Arzneimittel-Forschung, 25, pp. 681–708, (1975).

*Primary Examiner*—Thomas A. Waltz
*Attorney, Agent, or Firm*—Murray, Whisenhunt and Ferguson

[57] ABSTRACT

Nitrobenzoic acid amide derivative represented by the formula

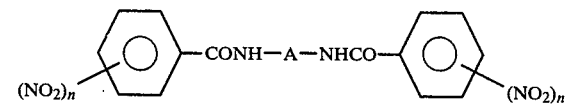

wherein A is $(CH_2)_x NH(CH_2)_y$ or $(CH_2)_x NH(CH_2)_y NH(CH_2)_z$, n is 1 or 2, x, y and z are each 2 to 5, and pharmacologically acceptable acid salt thereof is an excellent radio-sensitizer.

6 Claims, 1 Drawing Figure

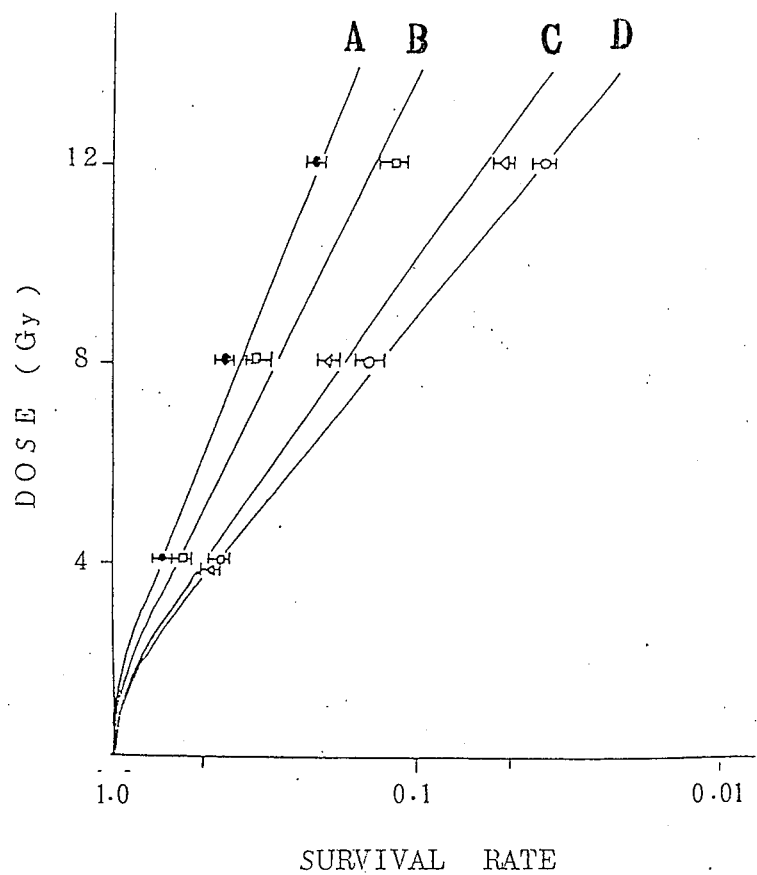

RADIOSENSITIZING NITROBENZOIC ACID AMIDE DERIVATIVES

The present invention relates to novel nitrobenzoic acid amide derivatives, process for preparing the same and radiosensitizer containing the same.

The radiotherapy is evaluated in great extents as well as the surgical treatment and chemotherapy in cancer treatments. However, it is difficult to destroy cancer tissues perfectly only by exposure to the radiation since hypoxic cells in solid tumors are strongly resistant to the radiation. Therefore, extensive research has been conducted on drugs which enhance the radiosensitivity to the hypoxic cells, namely radiosensitizer. For example, nitroimidazole derivatives such as misonidazole, metronidazole, etc. are known as the radiosensitizer. Most of the known radiosensitizer have drawbacks of still being remained to be improved in their radiosensitivity enhancing effects and having nervous toxicities.

The present inventors synthesized many compounds and investigated their pharmacological actions in order to obtain compounds having excellent radiosensitivity enhancing effects and found that novel nitrobenzoic acid amide derivatives of the formula (I) and pharmacologically acceptable acid salts thereof have excellent radiosensitivity enhancing effects.

Novel nitrobenzoic acid amide derivatives of the invention are represented by the formula

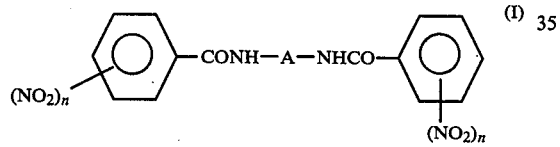

wherein A is $(CH_2)x\ NH(CH_2)y$ or $(CH_2)x\ NH(CH_2)y\ NH(CH_2)z$, n is 1 or 2, x, y and z are each 2 to 5.

Typical nitrobenzoic acid amide derivatives of the invention are given below.

(1) $N^1,N^{10}$-Bis(2-nitrobenzoyl)spermidine
(2) $N^1,N^{10}$-Bis(3-nitrobenzoyl)spermidine
(3) $N^1,N^{10}$-Bis(4-nitrobenzoyl)spermidine
(4) $N^1,N^{14}$-Bis(2-nitrobenzoyl)spermine
(5) $N^1,N^{14}$-Bis(3-nitrobenzoyl)spermine
(6) $N^1,N^{14}$-Bis(4-nitrobenzoyl)spermine
(7) $N^1,N^{13}$-Bis[3-(4-nitrobenzoyl)aminopropyl]-1,3-propanediamine
(8) $N^1$-[2-(4-Nitrobenzoyl)aminoethyl]-$N^4$-[3-(4-nitrobenzoyl)aminopropyl]-1,4-butanediamine
(9) $N^1$-(4-Nitrobenzoyl)-$N^2$-[4-(4-nitrobenzoyl)aminobutyl]-1,2-ethanediamine
(10) Bis-[4-(4-nitrobenzoyl)aminobutyl]amine
(11) $N^1,N^{10}$-Bis(2,4-dinitrobenzoyl)spermidine
(12) $N^1,N^{10}$-Bis(3,4-dinitrobenzoyl)spermidine
(13) $N^1,N^{10}$-Bis(3,5-dinitrobenzoyl)spermidine
(14) $N^1,N^{14}$-Bis(3,4-dinitrobenzoyl)spermine
(15) $N^1,N^{14}$-Bis(3,5-dinitrobenzoyl)spermine.

The novel compounds of the invention are prepared by, for example, reacting nitrobenzoic acids of the formula

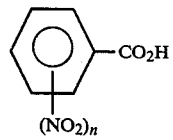

wherein n is as defined above and reactive derivatives thereof with polyamines of the formula $$H_2N—A—NH_2 \quad (III)$$

wherein A is as defined above.

Examples of the reactive derivatives of nitrobenzoic acids are an acid anhydride, acid halide, active ester, active amide of nitrobenzoic acid. The acid anhydride of nitrobenzoic acid is prepared by a usual method, for example, by the reaction of nitrobenzoic acid of the formula (II) and acetic anhydride. Examples of nitrobenzoic acid halides are bromide, chloride, etc. and chloride is preferable. The halides are also prepared by a usual method, for example, by the reaction of nitrobenzoic acid of the formula (II) with chlorinating agent such as thionyl chloride or phosphorus pentachloride. Examples of active esters of nitrobenzoic acid are N-hydroxysuccinimide ester, N-phthalimide ester, N-hydroxypiperidine ester, 8-hydroxyquinoline ester, 2-hydroxyphenyl ester, 2-hydroxypyridine ester, 2-pyridylthiol ester and p-nitrophenyl ester of nitrobenzoic acid. Preferable ester is N-hydroxysuccinimide ester of nitrobenzoic acid represented by the formula

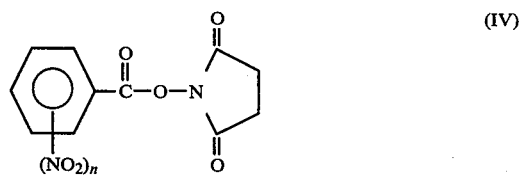

wherein n is as defined above. This compound is prepared by a usual method, e.g., by the reaction of nitrobenzoic acid of the formula (II) and N-hydroxysuccinimide in the presence of a condensing agent such as dicyclohexylcarbodiimide.

Examples of active amides of nitrobenzoic acid are 3-acyl-1,3-thiazolidine-2-thione, 3-acyl-2-oxazolone, etc. Preferable amide is 3-acyl-1, 3-thiazolidine-2-thione represented by the formula

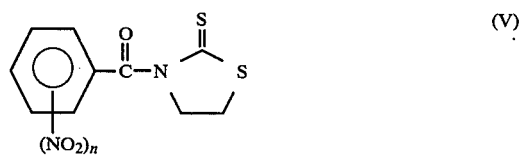

wherein n is as defined above. This compound is prepared by a usual method, for example by the reaction of nitrobenzoic acid of the formula (II) and 1, 3-thiazolidine-2-thione in the presence of a condensing agent such as dicyclohexylcarbodiimide, or by the reaction of nitrobenzoic acid chloride and 1, 3-thiazolidine-2-thione in the presence of organic base such as triethyl amine, dimethylaniline and pyridine or inorganic base such as potassium carbonate.

Examples of nitrobenzoic acids useful as a reactant component of the invention are o-nitrobenzoic acid, m-nitrobenzoic acid, p-nitrobenzoic acid, 2,4-dinitrobenzoic acid, 3,4-dinitrobenzoic acid and 3,5-dinitrobenzoic acid. Examples of polyamines of the formula (III) are spermine, spermidine, $N^1,N^3$-bis(3-aminopropyl)-1,3-propanediamine, $N^1$-(2-aminoethyl)-$N^4$-(3-aminopropyl)-1,4-butanediamine, N-(4-aminobutyl)-1,2-ethanediamine and bis(4-aminobutyl)amine.

The proportions of the nitrobenzoic acid of the formula (II) or reactive derivatives thereof and the polyamine of the formula (III) are suitably selected. Generally it is preferable to use about at least 2 equivalents, preferably about 2 to 2.2 equivalents of the former per equivalent of the latter. If desired, the reaction is accelerated by the addition of the condensing agent, organic or inorganic base used in the preparation of the aforementioned active ester and active amide. The amounts of the condensing agent, organic and inorganic base to be used are variable depending on the reaction conditions, etc. Generally it is preferable to use these compounds in an equimolar amount of the nitrobenzoic acid. The reaction of the invention may be conducted in the presence of solvents. Examples of useful solvents are chloroform, dichloromethane and like halogenated hydrocarbons, benzene, tolune and like aromatic hydrocarbons, dioxane, tetrahydrofuran, diethylene glycol dimethyl ether and like ethers, dimethylformamide, acetonitrile and like aprotic polar solvent, etc. Although the reaction temperature is not critical, it is preferred to effect the reaction usually under ice-cooling to 160° C., preferably at a temperature from room temperature to 50° C. The reaction time is also variable and is usually in the range of 2 to 15 hours, preferably 5 to 10 hours. After the reaction is completed, the desired compound of the invention is obtained by adding water to the reaction mixture and filtering the resulting crystals or by distilling off the solvent from the reaction mixture and subjecting the resulting residue to a column chromatography. If desired, the present compound can be purified by recrystallization and the like.

Nitrobenzoic acid amide derivatives of the formula (I) can be converted into pharmacologically acceptable acid salts by the treatment with inorganic or organic acids in methanol, ethanol and like alcohol or water. Examples of inorganic acids are hydrochloric acid, hydrobromic acid, sulfuric acid, nitric acid and phosphoric acid. Suitable organic acids are citric acid, maleic acid, malic acid, fumaric acid, succinic acid, methanesulfonic acid and p-toluenesulfonic acid.

The compounds of the formula (I) and pharmacologically acceptable acid salts thereof have excellent radiosensitivity enhancing effects to cells in hypoxic conditions and are useful as a radiosensitizer, anti-cancer agent, anti-microbial agent, protozoacide and like drugs.

The present compounds can be administered in the desired form of preparation in accordance with the therapy contemplated. They are provided for example as oral administration, injections or suppositories. These preparations can be formulated with a method already known in the art.

The present compounds can be admixed with carriers and, if desired, further with binder, disintegrator, glazing agent, coloring agent, flavoring agent and the like, and formulated into tablets, coated tablets, granules, powder, capsules and the like for oral solid preparation by a usual manner.

The present compounds can be admixed with flavoring agent, buffer agent, stabilizer and the like, and formulated into solutions, syrup, dry syrup and the like for oral liquid preparation by a usual manner.

The present compounds can be admixed with pH adjusting agent, buffer agent, stabilizer, isotonizing agent, topical anesthetic and the like, and formulated into hypodermic, intramuscular or intravenous injection by a usual manner.

The present compounds can be admixed with carriers and, if desired, further with surfactants and the like, and formulated into suppositories by a usual manner.

The daily dose of the present compounds is not specifically limited but can be varied with a patient's age or symptom. The preferred daily doses for adult are usually 0.1 to 1.5 g/m² of body's surface area. The present compounds are useful as radiosensitizer and are administered divided in one to several times prior to the exposure to radiation.

For a better understanding of the invention Reference Examples and Examples are given below.

REFERENCE EXAMPLE 1

Preparation of
3-(4-nitrobenzoyl)-1,3-thiazolidine-2-thione

To a solution of 4-nitrobenzoyl chloride (3.1 g) and tetrahydrofuran (50 ml) were added 1,3-thiazolidine-2-thione (2.0 g) and triethyl amine (2.5 g). The mixture was stirred at 50° C. for 30 minutes under nitrogen atmosphere. The reaction mixture was filtered and the solvent was removed at a reduced pressure. To the residue was added water, and the solution is extracted with dichloromethane. The extract was washed with a saturated aqueous solution of sodium chloride and dried with use of Glauber's salt. The solvent was distilled off and the resulting crystals were purified by silica gel column chromatography (developer: dichloromethane) and recrystallized from dichloromethane to obtain 3.3 g of the desired compound as yellow needle crystals (yield 82.5%).

Melting point: 166°–167° C.;
Elementary analysis: $C_{10}H_8O_3N_2S_2$.

|  | C | H | N |
|---|---|---|---|
| Theor. (%) | 44.78 | 3.01 | 10.45 |
| Found (%) | 44.60 | 2.91 | 10.60 |

NMR spectrum: δ (CDCl₃); 3.51 (2H, t, J=8 Hz); 4.58 (2H, t, J=8 Hz); 7.78, 8.20 (each 2H, AB type, J=8 Hz).

REFERENCE EXAMPLE 2

Preparation of
3-(3,5-dinitrobenzoyl)-1,3-thiazolidine-2-thione

To 15 ml of dimethylformamide were dissolved 3,5-dinitrobenzoyl chloride (2.5 g) and 1,3-thiazolidine-2-thione (1.3 g). To the solution was added dropwise a solution of triethyl amine (1.2 g) and dimethylformamide (2 ml) under ice-cooling. The mixture was stirred under ice-cooling for 1 hour and at room temperature for 5 hours. The reaction mixture was filtered and the solvent was removed at a reduced pressure. To the residue was added water and the insolubles were filtered off. The filtrate was washed with cold methanol and then with ether to obtain crude crystals. Recrystallization from toluene gives 2.4 g of the desired compound as yellow needle crystals (yield 76.7%).

Melting point: 215°–216° C. (decomposition);
Elementary analysis: $C_{10}H_7O_5N_3S$.

|  | C | H | N |
|---|---|---|---|
| Theor. (%) | 42.71 | 2.51 | 14.94 |
| Found (%) | 42.68 | 2.48 | 15.01 |

NMR spectrum: δ (DMSO-$d_6$); 3.65 (2H, t, J=8 Hz); 4.61 (2H, t, J=8 Hz); 8.83~8.94 (3H, m).

REFERENCE EXAMPLE 3

Preparation of 4-nitrobenzoic acid N-hydroxysuccinimide ester

To 50 ml of tetrahydrofuran were dissolved 4-nitrobenzoic acid (1.7 g) and N-hydroxysuccinimide (1.4 g). To the solution was added with stirring 2.1 g of dicyclohexyl carbodiimide under ice-cooling. The mixture was reacted under ice-cooling for 2 hours and then allowed to stand over night at room temperature. The crystals separated out from the mixture. After the filtration, the crystals were washed with tetrahydrofuran. The washings were combined with the filtrate and the solvent was removed at a reduced pressure. To the residue was added ether and the mixture was filtered. Recrystallization from methanol gives 2.4 g of the desired compound as colorless needle crystals (yield 90.9%).

Melting point: 217° C.;
Elementary analysis: $C_{11}H_8O_6N_2$.

|  | C | H | N |
|---|---|---|---|
| Theor. (%) | 50.01 | 3.05 | 10.60 |
| Found (%) | 49.80 | 3.00 | 10.42 |

NMR spectrum: δ (DMSO-$d_6$); 2.93 (4H, s); 8.35, 8.47 (each 2H, AB type, J=9 Hz).

REFERENCE EXAMPLE 4

Preparation of 3,4-dinitrobenzoic acid N-hydroxysuccinimide ester

According to Reference Example 3, 3,4-dinitrobenzoic acid (2.5 g) and N-hydroxysuccinimide (1.6 g) were subjected to condensation reaction in the presence of 2.4 g of dicyclohexyl carbodiimide. The crude product was recrystallized from a mixture of dioxane and petroleum ether, giving 2.9 g of the desired compound as colorless platy crystals (yield 94.3%).

Melting point: 220°–221° C.;
Elementary analysis: $C_{11}H_7O_8N_3$.

|  | C | H | N |
|---|---|---|---|
| Theor. (%) | 47.66 | 2.55 | 15.16 |
| Found (%) | 47.38 | 2.50 | 15.00 |

NMR spectrum: δ (DMSO-$d_6$); 2.93 (4H, s); 9.02–9.19 (3H, m).

EXAMPLE 1

Preparation of $N^1,N^{10}$-bis(4-nitrobenzoyl)spermidine

To a solution of 3-(4-nitrobenzoyl)-1,3-thiazolidine-2-thione (0.8 g) and dichloromethane (25 ml) was added a solution of spermidine (0.22 g) and dichloromethane (25 ml) and the mixture was stirred at room temperature under nitrogen atmosphere. The reaction mixture was washed with 100 ml of 2% aqueous solution of NaOH and the 1,3-thiazolidine-2-thione was removed. The organic layer was washed with a saturated aqueous solution of sodium chloride and dried with use of Glauber's salt. The solvent was removed at a reduced pressure. The resulting light yellow crude crystals were recrystallized from ethanol, giving 0.65 g of the desired compound as yellow needle crystals (yield 98%).

Melting point: 126°–127° C.;
Elementary analysis: $C_{21}H_{25}O_6N_5$.

|  | C | H | N |
|---|---|---|---|
| Theor. (%) | 56.87 | 5.68 | 15.79 |
| Found (%) | 56.83 | 5.79 | 16.11 |

Mass spectrum: $M^+$ m/e 443.
NMR spectrum: δ (CDCl$_3$); 1.50–2.05 (6H, m); 2.56–2.82 (4H, m); 3.40–3.60 (4H, m); 8.01, 8.31 (each 4H, AB type, J=9 Hz).
IR spectrum: νmax (KBr) cm$^{-1}$; 3320, 1638, 1600, 1545, 1528.

The above compound (0.32 g) was dissolved in ethanol. To the solution was added 3 ml of ethanolic hydrogen chloride prepared by dissolving 8 g of hydrogen chloride gas into 80 ml of ethanol. The solvent was removed at a reduced pressure. The resulting crystals were recrystallized from ethanol, giving 0.25 g of a hydrochloride of the above compound as colorless needle crystals (yield 71.4%). Melting point is 167°–168° C.

EXAMPLE 2

Preparation of $N^1,N^{14}$-bis(4-nitrobenzoyl)spermine (a) According to Example 1, 6.2 g of 3-(4-nitrobenzoyl)-1,3-thiazolidine-2-thione was reacted with 2.2 g of spermine. The resulting product was recrystallized from an aqueous ethanol solution to obtain 4.0 g of the desired compound as light yellow needle crystals (yield 79.3%).

Melting point: 200°–203° C.;
Elementary analysis: $C_{24}H_{32}O_6N_6$.

|  | C | H | N |
|---|---|---|---|
| Theor. (%) | 57.59 | 6.44 | 16.79 |
| Found (%) | 57.10 | 6.32 | 16.40 |

FD-MS spectrum: $M^+ + 1$ m/e 501;
$^{13}$C-NMR spectrum: δ (DMSO$_6$-$d_6$); 22.5, 25.6, 36.5, 44.5, 45.9, 123.3, 128.6, 139.7, 148.9, 164.6.
NMR spectrum: δ (DMSO-$d_6$); 1.30–1.83 (8H, m); 2.50–2.70 (8H, m); 3.20–3.45 (4H, m); 8.50, 8.31 (each 2H, AB type, J=9 Hz).
IR spectrum: νmax (KBr) cm$^{-1}$; 3250, 1650, 1600, 1560, 1520, 1350, 1240, 1085, 710, 665.

(b) To a dispersion of 4-nitrobenzoic acid N-hydroxysuccinimide ester (1.1 g) and tetrahydrofuran (20 ml) was added a solution of spermine (0.5 g) and tetrahydrofuran (10 ml) with stirring at room temperature. The mixture was stirred at room temperature for 5 hours. The reaction mixture was poured into 200 ml of ice-water. The resulting crystals were filtered and recrystallized from an aqueous ethanol solution to obtain 0.84 g of the desired compound as light yellow needle crystals (yield 80%).

The above compound (0.5 g) was dispersed in 5 ml of water. With the addition of 0.5 ml of concentrated hydrochloric acid, crystals separate out. The crystals were filtered during cool and recrystallized from an aqueous ethanol solution, giving 0.45 g of a hydrochloric acid salt of the above compound as colorless needle crystals (yield 79.0%). Melting point is 255°–258° C. (decomposition).

EXAMPLE 3

Preparation of $N^1,N^{10}$-bis(3,5-dinitrobenzoyl)spermidine

According to Example 2, (b) 3,5-dinitrobenzoic acid N-hydroxysuccinimide ester (2.1 g) was reacted with spermidine (0.5 g). The resulting crude crystals were recrystallized from benzene to obtain 1.4 g of the desired compound as yellow needle crystals (yield 76.8%).

Melting point: 182°–184° C.;
Elementary analysis: $C_{21}H_{23}O_{10}N_7$.

|  | C | H | N |
|---|---|---|---|
| Theor. (%) | 47.47 | 4.35 | 18.38 |
| Found (%) | 46.98 | 4.38 | 18.02 |

FD-MS spectrum: M+ +1 m/e 534;

$^{13}$C-NMR spectrum: δ (DMSO$_6$-d$_6$); 23.0, 25.5, 25.9, 36.9, 39.0, 44.7, 46.4, 120.6, 127.4, 136.8, 137.0, 148.0, 161.9, 162.1.

IR spectrum: νmax (KBr) cm$^{-1}$; 3330, 1650, 1540, 1350, 1250, 1080, 635, 630.

The above compound (0.53 g) was dispersed in 5 ml of water and 0.5 ml of concentrated hydrochloric acid was added thereto. The resulting crystals were filtered and recrystallized from water, giving 0.43 g of a hydrochloride of the above compound as colorless needle crystals (yield 75.4%). Melting point is 121°–124° C. (decomposition).

EXAMPLE 4

Preparation of $N^1,N^{14}$-bis(3,5-dinitrobenzoyl)spermine (a) According to Example 1, 3-(3,5-dinitrobenzoyl)-1,3-thiazolidine-2-thione (3.6 g) was reacted with spermine (1.1 g). The resulting crystals (2.6 g) were dispersed in 10 ml of water and 2 ml of concentrated hydrochloric acid was added thereto. The resulting crystals were filtered during cool and recrystallized from an aqueous ethanol solution to obtain 2.4 g of a hydrochloride of the desired compound as colorless needle crystals (yield 71.9%).

Melting point: gradually decompose more than 270° C.; Elementary analysis: $C_{24}H_{30}O_{10}N_8 \cdot 2HCl$.

|  | C | H | N |
|---|---|---|---|
| Theor. (%) | 43.45 | 4.86 | 16.89 |
| Found (%) | 43.46 | 4.87 | 16.43 |

FD-MS spectrum: M+ +1 m/e 591;

$^{13}$C-NMR spectrum: δ (CF$_3$CO$_2$H+D$_2$O); 24.8, 28.2, 42.3, 50.8, 52.6, 127.0, 133.1, 141.8, 153.9, 171.3.

IR spectrum: νmax (KBr) cm$^{-1}$; 3340, 2950, 2800, 1670, 1540, 1350, 1300, 735, 725.

(b) According to Example 2, (b), 3,5-dinitrobenzoic acid N-hydroxysuccinimide ester (2.4 g) was reacted with spermine (1 g). The resulting crude crystals were treated according to the method mentioned in above (a) to obtain a hydrochloride. Recrystallization from an aqueous ethanol solution gives 3.1 g of the hydrochloride of the desired compound as colorless needle crystals (yield 93.5%).

Melting point: gradually decompose more than 270° C.

EXAMPLE 5

The following compounds were prepared according to Example 1.
* $N^1,N^{10}$-Bis(4-nitrobenzoyl)spermidine methanesulfonic acid salt
  M.P. 113°–115° C.
* $N^1,N^{10}$-Bis(4-nitrobenzoyl)spermidine acetic acid salt
  M.P. 128°–130° C.
* $N^1,N^{10}$-Bis(4-nitrobenzoyl)spermidine sulfuric acid salt
  M.P. 155°–156° C. (decomposition).
* $N^1,N^9$-Bis(4-nitrobenzoyl)dipropylenetriamine
  M.P. 150° C.
* $N^1,N^9$-Bis(4-nitrobenzoyl)dipropylenetriamine hydrochloride
  M.P. 233°–234° C.
* $N^1,N^7$-Bis(4-nitrobenzoyl)diethylenetriamine
  M.P. 188° C.
* $N^1,N^7$-Bis(4-nitrobenzoyl)diethylenetriamine hydrochloride
  M.P. 251°–252° C. (decomposition).
* $N^1,N^{10}$-Bis(4-nitrobenzoyl)triethylenetetramine
  M.P. 193°–194° C.
* $N^1,N^{10}$-Bis(4-nitrobenzoyl)triethylenetetramine hydrochloride
  M.P. 270°–272° C. (decomposition).

EXAMPLE 6

The following compounds were prepared according to Example 2, (b).
* $N^1,N^{10}$-Bis(2,4-dinitrobenzoyl)spermidine hydrochloride
  M.P. 264°–265° C.
* $N^1,N^{14}$-Bis(2,4-dinitrobenzoyl)spermine hydrochloride
  M.P. 239°–241° C. (decomposition).
* $N^1,N^7$-Bis(2,4-dinitrobenzoyl)diethylenetriamine hydrochloride
  M.P. 229°–230° C.
* $N^1,N^9$-Bis(2,4-dinitrobenzoyl)dipropylenetriamine hydrochloride
  M.P. 199°–200° C.

Given below are examples of pharmacological composition according to the invention.

| Preparation 1 | |
|---|---|
| $N^1,N^{10}$—Bis(4-nitrobenzoyl)spermidine | 200 mg |
| Crystalline cellulose | 40 mg |
| Lactose | 39 mg |
| Corn starch | 15 mg |
| Hydroxypropyl cellulose | 5 mg |
| Magnesium stearate | 1 mg |
| | 300 mg (per tablet) |

A tableted preparation was formulated from the above ingredients.

| Preparation 2 | |
|---|---|
| $N^1,N^{14}$—Bis(4-nitrobenzoyl)spermine | 450 mg |

| -continued | |
|---|---|
| Preparation 2 | |
| Crystalline cellulose | 37 mg |
| Lactose | 10 mg |
| Silicic acid anhydride | 1.5 mg |
| Magnesium stearate | 1.5 mg |
| | 500 mg (per capsule) |

An encapsulated preparation was formulated from the above ingredients.

| Preparation 3 | |
|---|---|
| $N^1,N^{10}$—Bis(3,5-dinitrobenzoyl) spermidine | 700 mg |
| Crystalline cellulose | 30 mg |
| Lactose | 120 mg |
| Corn starch | 120 mg |
| Hydroxypropyl cellulose | 25 mg |
| Magnesium stearate | 5 mg |
| | 1000 mg (per pack) |

A fine granular preparation was formulated from the above ingredients.

| Preparation 4 | |
|---|---|
| $N^1,N^{14}$—Bis(2,4-dinitrobenzoyl)spermidine hydrochloride | 500 mg |
| distilled water for injection | (suitable amount) |
| | 10 ml (per ampule) |

An injection was formulated from the above ingredients.

| Preparation 5 | |
|---|---|
| $N^1,N^{14}$—Bis(2,4-dinitrobenzoyl)spermidine hydrochloride | 5.0 g |
| White petrolatum | 25.0 g |
| Stearyl alcohol | 17.0 g |
| Propylene glycol | 12.0 g |
| Sodium laurylsulfate | 1.5 g |
| Methyl p-hydroxybenzoate | 0.025 g |
| Propyl p-hydroxybenzoate | 0.015 g |
| Purified water | (suitable amount) |
| | 100.0 g |

An ointment was formulated from the above ingredients.

| Preparation 6 | |
|---|---|
| $N^1,N^{10}$—Bis(4-nitrobenzoyl)triethylenetetramine | 500 mg |
| Witepsol W-35 (A trade name for suppository base material manufactured by Dynamite Nobel Co.) | 1500 mg |
| | 2000 mg (per piece) |

Suppositories were formulated from the above ingredients.

The present compounds were tested by the following method to determine radiosensitivity enhancing effect.

Radiosensitivity enhancing effect to hypoxic cells

The test was conducted according to Ohizumi et al method (Gann 71, 319–324 (1980)).

To tissues of HeLa S3, $2\times 10^5/0.5$ ml, were added the present compounds. To the mixture was introduced a gas mixture (95% $N_2$, 5% $CO_2$) and the mixture was brought into hypoxic conditions. The mixture was irradiated by the gamma ray of $^{60}Co$ in 4, 8 and 12 Gy. The tissues were washed with Hanks BSS to remove the compounds tested, and then planted to MEM containing 10% bovine serum. Survival rate was determined from numbers of colonies formed after 10 to 12 days.

A group in which hypoxic tissues not containing the present compound were exposed to radiation was made control. FIG. 1 shows a relation between control and the present preparation in respect of survival rate and irradiation dose with use of the compound of Example 1. Doses were read which required to reduce survival rate to 37% at the straight parts of the survival curve in respect of control (Do) and the present compound (Do') at each concentration.

Enhancement ratio (ER) was calculated from Do/Do'. The results were given in Table 1.

TABLE 1

| Compound | Concentration of Compound (mM) | Enhancement Ratio |
|---|---|---|
| $N^1,N^{10}$—Bis(4-nitrobenzoyl)spermidine hydrochloride | 0.1 | 1.18 |
| | 0.5 | 1.65 |
| | 0.1 | 2.10 |
| $N^1,N^{14}$—Bis(4-nitrobenzoyl)spermine hydrochloride | 1.0 | 1.45 |
| Misonidazole | 0.1 | 1.05 |
| | 0.5 | 1.12 |
| | 1.0 | 1.32 |

FIG. 1 is a graph showing a relation between radiation dose and survival rate when radiation is applied to HeLa S3 tissues in hypoxic conditions. A is a case in which the present compound is not added (control), B to D are cases in which $N^1,N^{10}$-bis(4-nitrobenzoyl)spermidine hydrochloride was added in an amount of 0.1 mM, 0.5 mM and 1.0 mM respectively.

We claim:

1. Nitrobenzoic acid amide derivatives represented by the formula

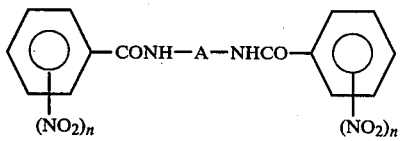

wherein A is $(CH_2)_x NH(CH_2)_y$ or $(CH_2)_x NH(CH_2)_y NH(CH_2)_z$, n is 1 or 2, x, y and z are each 2 to 5, and pharmacologically acceptable acid salts thereof.

2. $N^1,N^{10}$-Bis(4-nitrobenzoyl)spermidine and pharmacologically acceptable acid salt thereof according to claim 1.

3. $N^1,N^{14}$-Bis(4-nitrobenzoyl)spermine and pharmacologically acceptable acid salt thereof according to claim 1.

4. $N^1,N^{10}$-Bis(3,5-dinitrobenzoyl)spermidine and pharmacologically acceptable acid salt thereof according to claim 1.

5. $N^1,N^{14}$-Bis(3,5-dinitrobenzoyl)spermine and pharmacologically acceptable acid salt thereof according to claim 1.

6. A radiosensitizer composition comprising a radiosensitizing amount of a compound of claim 1 and a pharmaceutically acceptable carrier therefor.

* * * * *